United States Patent
Costo Lucco et al.

(10) Patent No.: US 11,980,779 B2
(45) Date of Patent: May 14, 2024

(54) COSMETIC ARTICLE IN STICK FORM AND A METHOD FOR MAKING IT

(71) Applicant: CHROMAVIS S.p.A., Offanengo (IT)

(72) Inventors: Davide Costo Lucco, Castelleone (IT); Stefano Luca Indaco, Offanengo (IT)

(73) Assignee: CHROMAVIS S.P.A., Offanengo (IT)

( * ) Notice: Subject to any disclaimer, the term of this patent is extended or adjusted under 35 U.S.C. 154(b) by 0 days.

(21) Appl. No.: 17/949,268

(22) Filed: Sep. 21, 2022

(65) Prior Publication Data
US 2023/0089917 A1  Mar. 23, 2023

(30) Foreign Application Priority Data
Sep. 21, 2021  (IT) .................. 102021000024155

(51) Int. Cl.
| | | |
|---|---|---|
| *A61Q 1/06* | (2006.01) | |
| *A61K 8/02* | (2006.01) | |
| *A61K 8/81* | (2006.01) | |
| *A61K 8/90* | (2006.01) | |

(52) U.S. Cl.
CPC .............. *A61Q 1/06* (2013.01); *A61K 8/0229* (2013.01); *A61K 8/8111* (2013.01); *A61K 8/90* (2013.01); *A61K 8/0233* (2013.01); *A61K 2800/10* (2013.01); *A61K 2800/48* (2013.01); *A61K 2800/882* (2013.01); *A61K 2800/95* (2013.01)

(58) Field of Classification Search
CPC .......... A61Q 1/06; A61Q 1/02; A61K 8/0229; A61K 8/8111; A61K 8/90; A61K 8/0233; A61K 2800/10; A61K 2800/48; A61K 2800/882; A61K 2800/95
USPC ....................... 401/16, 19, 22, 49, 52, 68, 72
See application file for complete search history.

(56) References Cited

U.S. PATENT DOCUMENTS

| | | | | |
|---|---|---|---|---|
| 4,740,097 | A * | 4/1988 | Kapustin | A45D 40/06 401/35 |
| 4,743,443 | A * | 5/1988 | Pisani | A61K 8/02 424/DIG. 5 |
| 6,695,510 | B1 * | 2/2004 | Look | A61K 8/0229 401/72 |
| 2005/0175573 | A1 | 8/2005 | Pagnoux et al. | |
| 2013/0171218 | A1 | 7/2013 | Bui et al. | |
| 2018/0200176 | A1 | 7/2018 | Li et al. | |

FOREIGN PATENT DOCUMENTS

JP        2017119698 A        7/2017

* cited by examiner

*Primary Examiner* — David J Walczak
(74) *Attorney, Agent, or Firm* — Dickinson Wright PLLC; Andrew D. Dorisio

(57) ABSTRACT

The invention describes a cosmetic article, in particular for make-up, in stick form comprising a transparent external product and a liquid internal product in which solid decorative elements are dispersed. The cosmetic article features an attractive, original appearance, which can be appreciated from both an aesthetic and a functional point of view upon application thereof to skin.

12 Claims, 2 Drawing Sheets

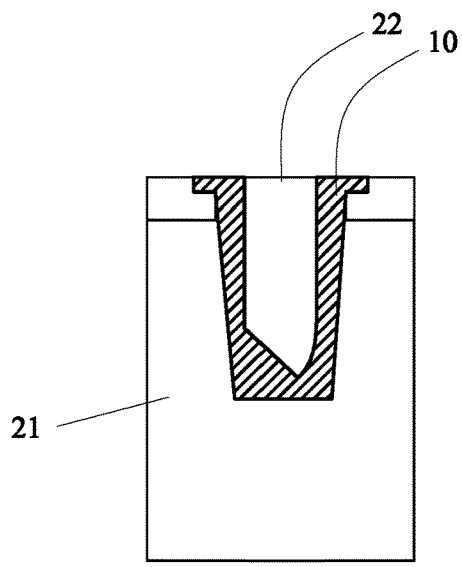
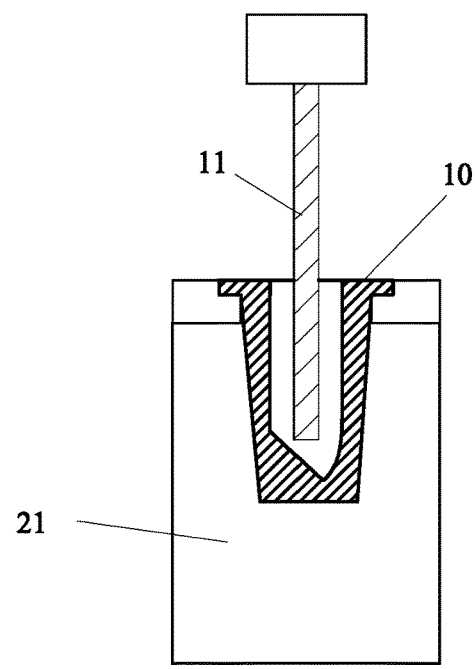
FIG.1　　　　　　FIG.2
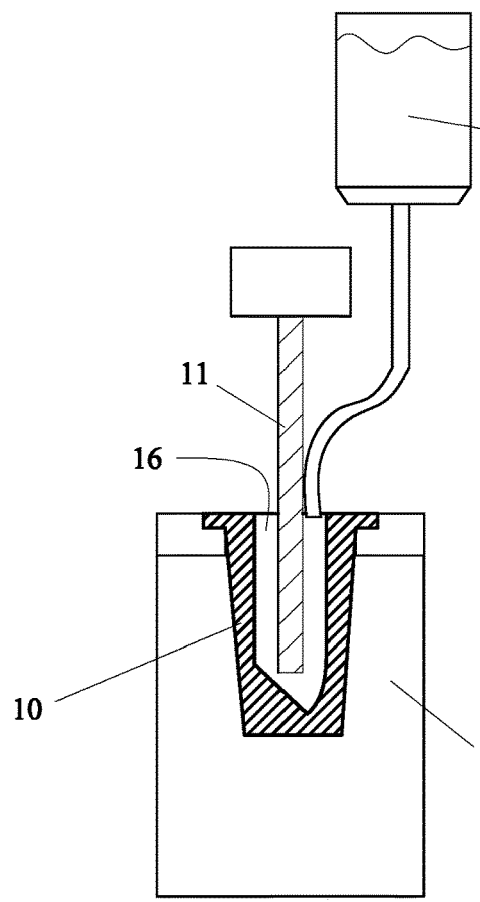
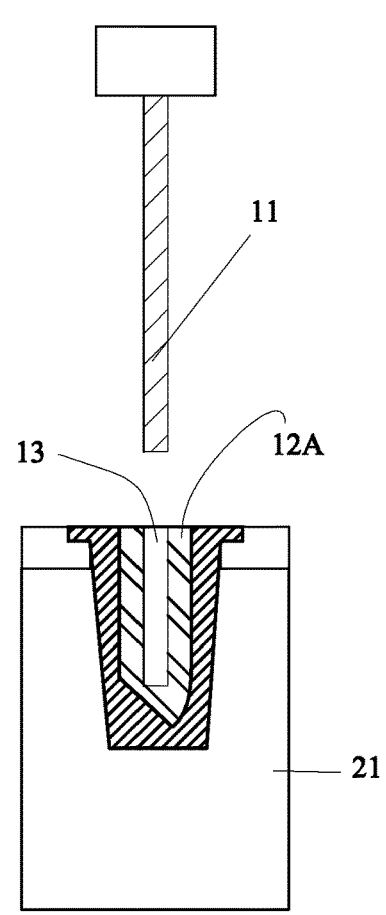
FIG.3　　　　　　FIG.4

COSMETIC ARTICLE IN STICK FORM AND A METHOD FOR MAKING IT

This application claims priority to Italian Patent Application for Invention No. 102021000024155 filed on Sep. 21, 2021, the disclosure of which is hereby incorporated by reference.

FIELD OF THE INVENTION

The present invention relates to a cosmetic article, in particular for make-up, and to a method for making it.

More specifically, it refers to an article in stick form, for example with a diameter which varies starting from 10 mm, such as a product for lips, eyes, face, or body, for example and in more detail: a lipstick, a lip balm, a foundation, a concealer, a primer, an eyeshadow, a blusher, a highlighter, a bronzer, or a deodorant.

BACKGROUND ART

Many cosmetic articles, in particular articles for make-up, are marketed in stick form, i.e. in a cylindrical form, in the form of a tube with a twist-up and down mechanism, and are therefore solid (think of lipsticks, lip balms, foundations, and deodorants, among others). This format has the advantage of making the cosmetic easier to use, as you can apply it more accurately in the desired area, without touching the cosmetic product with your hands.

In order to attract consumers, in addition to improving the functionality of these articles, there is increasing attention to the aesthetics thereof. Over time, therefore, cosmetic articles have been designed which are increasingly attractive to the consumer and/or which create particular aesthetic effects when applied.

Influenced by constantly changing trends, consumers are increasingly exacting and, indeed, look for products which are innovative, especially for make-up, provide original or specific visual effects, and are at the same time eye-catching in terms of the aesthetics of the said article, in order to encourage people to choose and purchase them.

Stick cosmetics that meet these needs are, for example, lipsticks with a shimmering effect (also referred to as "glitter"), obtained by incorporating fragments of various iridescent or pearlescent materials into the bulk product. There are also varyingly transparent cosmetic sticks available on the market that include decorative elements in different shapes, for example in the shape of a flower, a heart, or a star etc., which are visible externally.

There are also commonly known products, such as lip gloss, i.e. a transparent gel featuring varying degrees of colour, within which the said glitter may be dispersed. Depending on the consistency of the gel, lip gloss can be produced in various forms. In particular, more liquid formulations can be packaged in a bottle, for example, equipped with a soft, spongy applicator or with a roll-on applicator, or in a rigid case (made of glass or plastic) with a wand applicator. The more solid formulations may be presented in the form of sticks with various diameters or contained in a jar. To apply the latter form, it is necessary to use a suitable applicator (brush, sponge, etc.), or dab your fingers on the product and then apply it in the desired area.

Although the latter is clearly more attractive from an aesthetic and commercial point of view, it must nevertheless be considered that more liquid lip glosses are also those that tend to stay on less, because—unlike lipsticks—they generally do not have a waxy structure.

SUMMARY OF THE INVENTION

The object of the present invention is to produce a cosmetic article, in particular for make-up or skin-care, which is improved with respect to the known art.

This and other objects are achieved by means of a cosmetic article, in particular for make-up according to the technical teachings of the claims annexed hereto.

One advantage of the cosmetic article, in particular for make-up, according to the invention is, therefore, to offer appealing aesthetic properties, through decorative elements which are made dynamic by the suspension thereof in a fluid product, the said article maintaining, however, the advantages of solid stick products.

A further advantage is the possibility of conveying water-soluble active ingredients and/or fat-soluble dyes in aqueous matrices and/or water-soluble dyes by means of the stick.

BRIEF DESCRIPTION OF THE FIGURES

Further characteristics and advantages of the invention will become clearer in the description of a preferred but not exclusive embodiment of the invention, illustrated—by way of a non-limiting example—in the drawings annexed hereto, in which:

FIG. 1 is a schematic, sectional side view of a mould which can be used to form the stick;

FIGS. 2 to 7 show schematically, and again as section views, various steps in the making of the stick according to the invention.

DETAILED DESCRIPTION OF THE INVENTION

Figure 5:
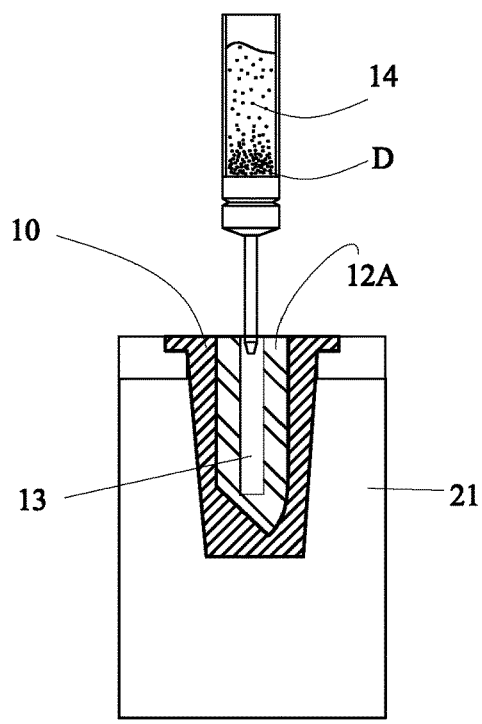
Figure 6:
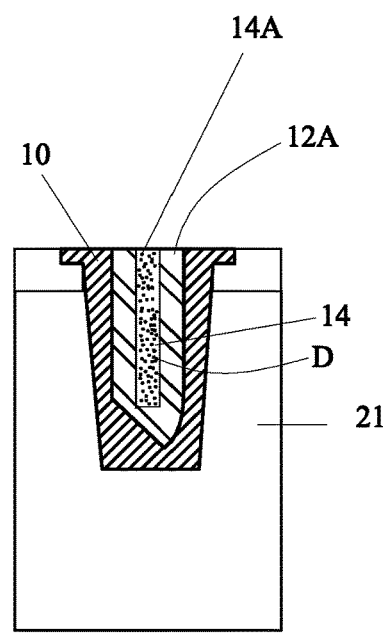

The present invention therefore relates to a cosmetic article 20, in particular for make-up, in stick form comprising:
- a first cosmetic product 12A, in stick form, with an essentially solid or pasty consistency at room temperature, which defines at least one internal cavity 13; and
- a second cosmetic product 14, 14A housed in at least one internal cavity 13, the second cosmetic product 14, 14A comprising:
  i) up to 95 wt % water, based on the weight of the second product 14, 14A,
  ii) a heat-sensitive viscosifying agent comprising poloxamers, and
  iii) solid decorative elements or a fat-soluble dye, or a combination thereof.

The first cosmetic product 12A is preferably transparent or translucent at room temperature in order to make the contents of the said internal cavity 13 visible from the outside to a user.

The first cosmetic product 12, 12A and the second cosmetic product 14, 14A are preferably make-up products, but they can also be functional products.

In the following description, when reference is made to the first cosmetic product 12, 12A, reference number 12 will be used when the said product is in liquid or in any case fluid form (i.e. fluid enough to be poured), therefore well above room temperature (for example at 65° C.).

When referring the second cosmetic product, however, reference number 14 will be used to denote the said product in liquid form, and reference 14A to denote the said product in solid/gel form, for example after the said product has been given structure through a rise in temperature.

The term "room temperature" here means a temperature of 20-25° C., preferably approximately equal to 25° C.

It has therefore surprisingly been found that it is possible to overcome the aforesaid technical problem by producing a cosmetic article in stick form in which a first cosmetic product 12A, preferably for make-up or for skin-care, in a solid or pasty form at room temperature (bulk) forms—at least in part—the outermost portion of the article and delimits—at least partially—a cavity containing a second product 14 in a liquid state, in which either solid decorative elements or a fat-soluble dye, or a combination thereof, are dispersed in a freely movable manner.

In particular, the presence of a heat-sensitive viscosifying agent comprising poloxamers (in the second product 14, 14A) has made it possible to exploit the aesthetic effects offered by the movement of the decorative elements and/or droplets of fat-soluble dye dispersed in a liquid matrix, at the same time preventing the latter coming out when the chamber 13 breaks during application of the stick to allow the elements contained therein out.

In fact, the heat-sensitive viscosifying agent that is liquid—or in any case very fluid—at room temperature tends, however, to gel (for example, on the surface denoted 14A) as the temperature increases, for example upon contact with the warmth of the skin.

Therefore, an article has been advantageously obtained that combines the properties and practicality of use of a conventional stick, such as a transparent/semi-transparent lipstick, with a dynamic aesthetic effect typical of a liquid formulation (e.g. a conventional lip gloss in which glitter is dispersed, floating freely therein) and/or a functional effect linked to the addition of fat-soluble dyes to the containment chamber 13 which form coloured droplets upon contact with the aqueous matrix.

The second product 14 comprises up to 95 wt % water, as well as a heat-sensitive viscosifying agent capable of forming a gel therewith at temperatures above room temperature. Preferably at temperatures of 32-40° C., the said heat-sensitive viscosifying agent turns the water completely to gel, thereby making the second product solid in the outermost portion of the chamber and preventing the said water/gel from coming out (essentially acting as a plug or plug layer).

The temperature of 32-40° C. is essentially the temperature reached by the second product 14 when, during use, it comes into contact with the user's skin.

In this way, in the article according to the invention, the second product 14 contained in the cavity 13 of the body inside the first product 12, 12A, is in a liquid state at room temperature and the decorative elements/fat-soluble dyes can be suspended and move therein. During use of the article, that is, during application to the skin or lips, as the first product gradually wears out and thins and therefore the second product emerges, a combined effect of the two products (possibly a make-up effect) is obtained. Meanwhile, the warmth of the skin or lips has increased the temperature of the second product; therefore, as soon as application is complete, the said product gels, thereby preventing the latter coming out of the article.

It must be said that once the second product 14A has gelled through an increase in temperature or contact with air, the said product maintains the consistency of gel even if the temperature thereof drops, returning to room temperature. The layer of the gelled second product 14A then isolates the still liquid second product 14 contained in the cavity 13, keeping the said product in a liquid state.

Preferably, the heat-sensitive viscosifying agent has a viscosity of 10-60 mPa·s at room temperature and a viscosity of 30-70 Pa·s at 45° C.

As mentioned above, the heat-sensitive viscosifying agent comprises poloxamers.

Poloxamers are non-ionic triblock copolymers composed of a central hydrophobic chain of polyoxypropylene (poly (propylene oxide)) flanked by two hydrophilic chains of polyoxyethylene (poly(ethylene oxide)). Since the lengths of the polymer blocks can be customised, there are multiple poloxamers with slightly different properties. These copolymers are commonly referred to with the letter P (standing for poloxamer) followed by three digits.

One characteristic of the poloxamer solutions that can be important is the self-assembling and heat-gelling behaviour thereof, which is linked to changes in temperature. Concentrated aqueous solutions of poloxamers are liquid at low temperatures and solidify at higher temperatures. The transitions that occur in these systems depend mainly on the composition of the polymer (molecular weight and hydrophilic/hydrophobic molar ratio).

At low temperatures and concentrations (below the critical micelle temperature and the critical micelle concentration) single block copolymers (unimers) are present in solution. Above these values, aggregation of the individual unimers occurs through a process called micellisation. This aggregation is caused by the dehydration of the hydrophobic block of polyoxypropylene, which becomes progressively less soluble as the polymer concentration or temperature increases. The aggregation of different unimers occurs to minimise interactions between the PPO blocks and the solvent. Therefore, the core of the aggregates is made up of the insoluble blocks (polyoxypropylene) while the soluble portion (polyoxyethylene) forms the shell of the micelles.

Suitable poloxamers are disclosed in U.S. Patent Application n. US2005/175573 A1.

The second product 14 preferably comprises the said poloxamer at a concentration of 0.2-15 wt %, more preferably 0.4-12 wt %, even more preferably 1-10 wt %, based on the weight of the second product.

In preferred embodiments, in the viscosifying agent, the said poloxamer is Poloxamer 338 (CAS: 9003-11-6).

In particularly preferred embodiments, the said viscosifying agent includes Poloxamer 338 and a PPG/SMDI copolymer, where PPG is polypropylene glycol and SMDI is methylene diphenyl diisocyanate aliphatic.

In the most preferred embodiments, the Poloxamer 338 and the PPG/SMDI copolymer are in a weight ratio of 2:1 to 10:1.

The embodiments in which the said viscosifying agent consists of 70-90 wt % Poloxamer 338 and 10-30 wt % PPG-51/SMDI copolymer are particularly preferred.

Preferably, the second cosmetic product 14, 14A comprises 50-80 wt % water, based on the weight of the second product.

Optionally, the second product 14 further comprises a water-miscible solvent, more preferably an alcoholic solvent, such as ethanol.

As mentioned above, the second product 14 also comprises iii) decorative solid elements or fat-soluble dye, or a combination thereof.

Preferably, the second product 14 comprises up to 35 wt %, based on the weight of the second product, of iii) decorative solid elements, or fat-soluble dye, or a combination thereof, more preferably 1-30 wt %.

The term "solid decorative element" is understood as comprising decorative elements such as pigments, either as they are or on a solid medium, in the form of small spheres or glitter.

The term "spheres" or "small spheres" includes not only perfectly spherical solid forms but also solids which are essentially spherical in shape or are similar to spheres in shape, such as spheroids.

Preferably, the decorative solid elements dispersed in the second product can have essentially the same diameter or the same shape or different diameters or shapes. The choice depends on the aesthetic effect desired for the end article.

The said solid decorative elements can also be pearlescent pigments on substrates, such as preferably: natural or synthetic mica (fluorphlogopite), calcium sodium borosilicate, calcium aluminium borosilicate, or calcium titanium borosilicate, silica.

The said solid decorative elements can also be, as mentioned above, glitter, for example synthetic glitter, made of: polyethylene terephthalate, epoxy resin copolymer, isobutylphenoxy-acrylate, polyethylene terephthalate-polybutylene terephthalate, isobutylphenoxy epoxy resin, polyethylene terephthalate-polyurethane-11, polyethylene terephthalate, or natural glitter (bioglitter), for example bioglitter made of: rayon, cellulose acetate.

The said solid decorative elements can also be pigments or pigment substrates, such as, preferably: iron oxides (INCI: CI 77492, CI 77499, CI 77491), titanium oxide (CI 77891), manganese violet (CI 77742), ultramarine (CI 77007), chromium oxide green (CI 77288), chromium hydroxide green (INCI: CI 77289), red sodium salt 6 (CI 15850), yellow lacquer 5 (CI 19140), red lacquer 22 (CI 45380), red lacquer 21 (CI 45380), red 7 (CI 15850), red lacquer 7 (CI 15850), lacquer red 40 (CI 16035), carmine (CI 75470), lacquer red 28 (CI 45410), lacquer red 27 (CI 45410), lacquer yellow 6 (CI 15985), iron ammonium ferrocyanide (CI 77510), lacquer red 30 (CI 73360), lacquer blue 1 (CI 42090), aluminium powder (CI 77000) in pure form or dispersed in mineral carriers, such as talc or mica.

The term "fat-soluble dye" refers to one or more lipophilic dyes which, as such, are insoluble in water and therefore form coloured droplets therein.

Suitable fat-soluble dyes can be either natural in origin, such as castor oil, or synthetic in origin, such as octyldodecanol and octyldodecyl stearoyl stearate.

Optionally, water-soluble dyes can also be added to the water of the second product 14, which can therefore create a pleasant chromatic contrast with either the solid decorative elements or the fat-soluble dye, or with a combination thereof.

Suitable water-soluble dyes are, for example, CI 19140 [YELLOW 5] 100%, CI 15985 [YELLOW 6] 100%, CI 42090 [BLUE 1] 100%, CI 17200 [RED 33] 100%, CI 45410 [RED 27] 100%, CI 45410 [RED 28] 100%, CI 45380 [RED 22] 100%, CI 45380 [RED 21] 100%).

In preferred embodiments, the second product 14 further comprises water-soluble active ingredients, such as vitamins (in particular vitamin C), botanical extracts, antimicrobial agents, anti-irritation agents, humectants, antioxidant agents, moisturising agents, UV-ray absorbing agents, and mixtures thereof.

According to particularly preferred aspects, the first product 12 is transparent or translucent and either coloured or colourless. Preferably, the said first product is a solid gel comprising a lipid matrix and a gelling agent which can form a network of microscopic fibres in the lipid matrix, producing a solid, completely transparent gel during cooling.

Preferably, the said lipid matrix comprises, or essentially consists of, one or more of the following: tridecyl trimellitate, hydrogenated polyisobutene, and/or octyldodecanol.

Preferably, the said gelling agent comprises, or essentially consists of, a mixture of: dibutyl ethyl hexanoyl glutamide, dibutyl lauroyl glutamide, dispersed in the lipid matrix, preferably in a lipid matrix comprising, or consisting of, a polar ester, such as an octyldecanol ester.

Preferably, the said first product further comprises one or more of the following (dissolved or suspended in the said lipid gel): lipophilic active ingredients, flavourings, aromas, suspended elements, and pigments. The latter may be as described above with reference to the second product.

Optionally, the said first product can further comprise at least one water-miscible solvent, more preferably an alcoholic solvent, such as ethanol.

Particularly preferred cosmetic articles in stick form according to the invention may include: lip sticks, such as lipsticks, balms, or glosses, sticks for eye and face use, such as eye shadows, foundations, concealers, primers, bronzers, blushers, highlighters, and sticks for body use, such as deodorants.

The physical properties of the second product are particularly advantageous also for the preparation of the article according to the invention, since the second product can be advantageously poured into the internal cavity 13 of the first solidified product, since the said second product is liquid at room temperature, as detailed below.

From a different perspective, the present invention also relates to a process for preparing the cosmetic article as described above. This process comprises the following steps:

i. providing a mould 10 comprising a cavity 22;
ii. inserting a core 11 into the cavity 22 in the mould 10, so as to determine a first casting cavity 16 between the walls of the mould 10 which determine the cavity 22 and the outer perimeter of the core 11;
iii. pouring a first cosmetic product 12 into the first casting cavity 16 and waiting for the said first product to solidify;
iv. extract the core 11 once the first cosmetic product 12 has solidified, so that the portion of the first solidified cosmetic product 12A that housed the core 11 determines an internal cavity 13 within the first solidified cosmetic product 12A;
v. pouring a second cosmetic product 14 in an essentially liquid form into the internal cavity 13, the second cosmetic product 14 comprising up to 95 wt % water (based on the weight of the second product), a heat-sensitive viscosifying agent comprising poloxamers, and either solid decorative elements or a fat-soluble dye, or a combination thereof, dispersed in the second cosmetic product 14;
vi. isolating the second cosmetic product 14 within the internal cavity 13, and
vii. removing the cosmetic article 20 from the mould.

Advantageously, the mould 10 can be made (at least partially) of silicone or another material which is suitable for forming a stick (for example, another elastic material or even metal and/or ceramic).

It can be housed or positioned in a vacuum chamber 21, which can apply a vacuum to the outside of the mould in order to remove a stick 20 made using the mould 10 therefrom.

Before inserting the mould, the core 11 can be covered with a mould release agent. Alternatively, the said core can be made of a self-lubricating material that allows easy extraction thereof in order to form the internal cavity 13.

The first cosmetic product 12 can be heated to above room temperature prior to casting, until the said product takes on an essentially liquid consistency. For example, the first cosmetic product 12 is heated to approximately 65° C.

The first cosmetic product 12 inside the mould 10 can be cooled (for example, by cold air) to below room temperature in order to speed up solidification thereof.

The second cosmetic product 14 can be isolated inside the internal cavity 13 by exposing a surface thereof to a heat source in order to make a layer of the second cosmetic product 14A solid, or by solidifying the said exposed surface in any case.

Alternatively, it is possible to pour the first liquid cosmetic product 12 or another product which is solid at room temperature onto an exposed surface of the second cosmetic product 14.

The stick 20 can be removed from the mould according to conventional methods, for example by applying a vacuum to the inside of the vacuum chamber 21.

Before or during removal from the mould, it is possible to couple the stick 20 to a device 15 (for example, for lipsticks or deodorants).

Depending on the shape of the core 11 and the positioning thereof with respect to the mould 10, the internal cavity 13 can be delimited by a surface of the said mould 10 prior to filling. In this way, after extracting the stick 20, a (suitably solidified) part of the second product cosmetic 14 will be exposed to a surface of the stick 20 which is active (therefore usable for make-up).

Obviously, the internal cavity 13 can have a configuration corresponding to that of the core 11.

This configuration can have a cross section according to one of the following geometric forms: circle, ellipse, triangle, square, rectangle, heart shape, star shape.

The internal cavity 13 may extend along all or most of the final length of the stick 20.

Advantageously, the wall of the stick (formed of the first solidified cosmetic product 12A) will be thick enough to be able to effectively contain the second cosmetic product 14, which is liquid at room temperature, without breaking or getting damaged during normal use of the said stick 20.

FIGS. 1-7 show the steps for the preparation of a lipstick (therefore, in this case, the cosmetic article is a make-up article), according to preferred aspects of the present invention.

It should also be understood that all aspects identified as favourable and advantageous for the cosmetic article should be deemed equally preferable and advantageous also for the uses and the preparation process thereof.

It should likewise be understood that all combinations of the preferred aspects of the cosmetic article envisaged in the invention, as well as the uses and the preparation process thereof, as set out above, should be considered described herein.

The following section provides embodiment examples of the present invention for illustration purposes.

EXAMPLES

Example 1

A lipstick was prepared according to the present invention.

A first product 12 comprising the following composition was poured into the first casting cavity 16 in a mould 10, between the internal walls of the mould 10 and the external perimeter of a core 11:

| ingredient | wt % |
| --- | --- |
| OCTYLDODECANOL | 23 |
| DIBUTYL LAUROYL GLUTAMIDE | 3.50 |
| DIBUTYL ETHYLHEXANOYL GLUTAMIDE | 2.3 |
| TRIDECYL TRIMELLITATE | 39.2 |
| HYDROGENATED POLYISOBUTENE | 32 |
| total | 100 |

The first product 12 was heated enough to take on a liquid and therefore pourable consistency. More specifically, the first product was heated to 65° C. The core 11 has a lamellar shape, and therefore the cross section thereof is rectangular.

Once the first product 12A had solidified, the core 11 was extracted and a second product 14 comprising the following composition was poured into the internal cavity 13 thus formed (with a configuration corresponding to that of the core):

| Ingredient | wt % |
| --- | --- |
| Water | 70 |
| Poloxamer 338 | 8 |
| PPG-51/SMDI | 2 |
| Pigmented glitters/Dispersed pigments | 20 |
| Total | 100 |

The second product 14 was then isolated inside the internal cavity 13 by heating the free surface thereof, resulting in a surface layer thereof solidifying.

Figure 7:
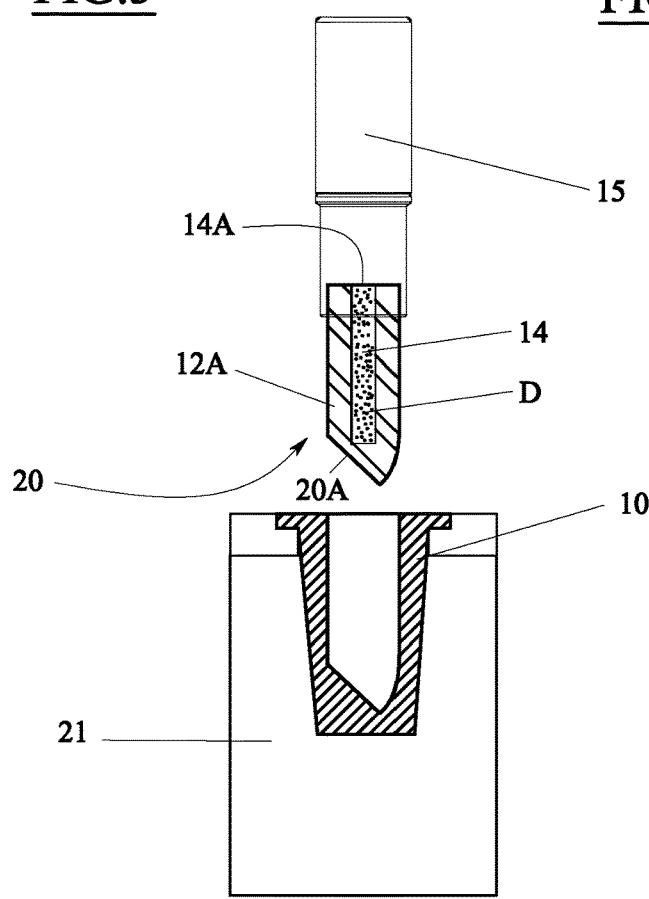

The cosmetic article 20 was then coupled with a device 15 and extracted from the mould 10 as shown in FIG. 7.

Example 2

A lip balm was prepared comprising the first product 12 in Example 1, poured into the first casting cavity of a mould between the internal walls of the mould and the outer perimeter of a core with a rectangular section.

Once the first product 12A had solidified, the core was extracted and a second product comprising the following composition was poured into the internal cavity 13 thus formed:

| Ingredient | wt % |
| --- | --- |
| Water | 60 |
| Poloxamer 338 | 7 |
| PPG-51/SMDI | 3 |
| Pigmented spheres | 30 |
| Total | 100 |

The second product 14 was completely incorporated into the first solidified product by pouring a layer of the first product 12 onto the exposed part of the second product 14 and waiting for the solidification of the layer of first product 12A.

The invention claimed is:

1. A cosmetic article (20) in the form of a stick comprising:
   a first cosmetic product (12A), in the form of a stick having a solid or pasty consistency at room temperature, which defines at least one internal cavity (13); and
   a second cosmetic product (14, 14A) housed in at least one internal cavity (13), the second cosmetic product (14, 14A) comprising:
   i) up to 95% by weight of water, based on the weight of the second product 14, 14A,
   ii) a heat sensitive viscosifying agent comprising poloxamer,
   iii) decorative solid elements, or fat-soluble dye, or a combination thereof, the first cosmetic product (12A), at room temperature, being transparent or translucent in order to make the contents of said internal cavity (13) visible from the outside to a user.

2. The article of claim 1, wherein said cavity (13) extends for at least half the length of said stick, an area of said internal cavity (13), in section, being less than the area of said first product, in section.

3. The article of claim 1, wherein the second product (14, 14A) comprises said poloxamer in a concentration of 0,2-15% by weight of the weight of the second product.

4. The article of claim 1, in which, in the viscosifying agent, said poloxamer is poloxamer 338.

5. The article of claim 1, wherein said viscosifying agent comprises poloxamer 338 and a PPG/SMDI copolymer.

6. The article of claim 5, in which said poloxamer 338 and copolymer PPG/SMDI are in a weight ratio from 2:1 to 10:1.

7. The article of claim 5, wherein said viscosifying agent comprises 70-90% by weight of said poloxamer 338 and 10-30% by weight of said PPG-51/SMDI copolymer.

8. The article of claim 1, in which said first product comprises:
   a lipid matrix, comprising one or more of: tridecyl trimellitate, hydrogenated polyisobutene or octyldodecanol,
   a gelling agent, comprising a mixture of dibutyl ethylhexanoyl glutamide and dibutyl lauroyl glutamide, dispersed in the lipid matrix.

9. A process for the preparation of a cosmetic article (20) comprising the steps of:
   a. providing a mold (10) comprising a cavity (22),
   ii. inserting a core (11) into the cavity (22) of the mold (10), so as to define a first casting cavity (16) between the walls of the mold (10) which define the cavity (22) and an external perimeter of the core (11),
   iii. pouring a first cosmetic product (12) into the first casting cavity (16) and wait for said first product to solidify,
   iv. once the first cosmetic product (12) has solidified, extracting the core (11), so that the portion of the first solidified product (12A) that housed the core (11) defines an internal cavity (13),
   v. pouring a second cosmetic product (14), in liquid form into the internal cavity (13), the second cosmetic product (14) comprising up to 95% by weight of water, based on the weight of the second product, a heat-sensitive viscosifying agent comprising poloxamer, and solid decorative elements, or fat-soluble dye, or a combination thereof, being dispersed in the second cosmetic product (14);
   vi. isolate the second liquid product (14) inside the internal cavity (13); and
   vii. unmold the cosmetic item (20) from the mold.

10. The process of claim 9, wherein the internal cavity (13), before being filled, opens on a surface of said mold (10).

11. The process of claim 9, wherein the internal cavity (13) has a cross section according to one of the following geometric figures: circle, ellipse, triangle, square, rectangle, heart-shaped, star-shaped.

12. The process of claim 9, in which the core (11) is sprinkled with lubricating agent before being inserted into the mold (10).

* * * * *